United States Patent
Isaka

(10) Patent No.: US 11,572,343 B2
(45) Date of Patent: Feb. 7, 2023

(54) PERFLUORO DIACYL PEROXIDE AS POLYMERIZATION INITIATOR AND POLYMER PREPARATION METHOD

(71) Applicant: DAIKIN INDUSTRIES, LTD., Osaka (JP)

(72) Inventor: Tadaharu Isaka, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 86 days.

(21) Appl. No.: 16/969,618

(22) PCT Filed: Jan. 25, 2019

(86) PCT No.: PCT/JP2019/002470
§ 371 (c)(1),
(2) Date: Aug. 13, 2020

(87) PCT Pub. No.: WO2019/159652
PCT Pub. Date: Aug. 22, 2019

(65) Prior Publication Data
US 2021/0032201 A1    Feb. 4, 2021

(30) Foreign Application Priority Data
Feb. 16, 2018   (JP) .............................. JP2018-026216

(51) Int. Cl.
*C07C 409/34* (2006.01)
*C08F 2/06* (2006.01)
*C08K 5/14* (2006.01)

(52) U.S. Cl.
CPC ............. *C07C 409/34* (2013.01); *C08F 2/06* (2013.01); *C08K 5/14* (2013.01)

(58) Field of Classification Search
CPC ........... C07C 409/34; C08F 2/06; C08K 5/14
USPC ...................................................... 526/231
See application file for complete search history.

(56) References Cited

U.S. PATENT DOCUMENTS

| | | | |
|---|---|---|---|
| 2,792,423 A | 5/1957 | Young et al. | |
| 4,411,843 A | 10/1983 | Anello et al. | |
| 5,831,131 A * | 11/1998 | Krespan | C07C 409/34 568/560 |
| 5,962,746 A * | 10/1999 | Diffendall | C07C 407/00 568/560 |
| 7,135,599 B2 * | 11/2006 | Navarrini | C07D 317/42 568/560 |
| 2002/0128411 A1 * | 9/2002 | Navarrini | C07D 317/42 562/2 |
| 2004/0198936 A1 * | 10/2004 | Navarrini | C08F 4/34 526/231 |

FOREIGN PATENT DOCUMENTS

| | | |
|---|---|---|
| CN | 102675519 A | 9/2012 |
| CN | 103265466 A | 8/2013 |
| CN | 104231228 A | 12/2014 |
| JP | 49-010290 A | 1/1974 |
| JP | 59-059643 A | 4/1984 |
| JP | 11-511464 A | 10/1999 |
| JP | 2002-332275 A | 11/2002 |
| WO | 97/08142 A1 | 3/1997 |

OTHER PUBLICATIONS

Hideo Sawada, "Fluorinated Peroxides", Chem. Rev., 1996, pp. 1779-1808, vol. 96.
International Search Report of PCT/JP2019/002470 dated Apr. 23, 2019 [PCT/ISA/210].
Extended European Search Report dated Oct. 19, 2021 in counterpart European Application No. 19754008.1.
International Preliminary Report on Patentability with translation of the Written Opinion dated Aug. 18, 2020 in International Application No. PCT/JP2019/002470.

* cited by examiner

*Primary Examiner* — Michael M. Bernshteyn
(74) *Attorney, Agent, or Firm* — Sughrue Mion, PLLC

(57) ABSTRACT

A perfluorodiacyl peroxide represented by the following formula (1):

$$(C_5F_{11}COO)_2 \qquad (1).$$

Also disclosed is a solution containing the perfluorodiacyl peroxide, a polymerization initiator containing the perfluorodiacyl peroxide, a method for producing a polymer which includes polymerizing a radically polymerizable monomer with the perfluorodiacyl peroxide, and a perfluoroacyl chloride represent by the following formula (2):

$$C_5F_{11}COCl \qquad (2).$$

2 Claims, No Drawings

PERFLUORO DIACYL PEROXIDE AS POLYMERIZATION INITIATOR AND POLYMER PREPARATION METHOD

CROSS REFERENCE TO RELATED APPLICATIONS

This application is a National Stage of International Application No. PCT/JP2019/002470, filed Jan. 25, 2019, claiming priority to Japanese Patent Application No. 2018-026216, filed Feb. 16, 2018.

TECHNICAL FIELD

The disclosure relates to perfluorodiacyl peroxides, solutions, polymerization initiators, methods of producing a polymer, and perfluoroacyl chlorides.

BACKGROUND ART

Fluorine-based diacyl peroxides are known as polymerization initiators.

For example, Non-Patent Literature 1 discloses synthesis of a perfluorodiacyl peroxide from a perfluoroacyl halide in the presence of $H_2O_2$ and NaOH.

Patent Literature 1 discloses production of bis(perfluoro-n-butyryl)peroxide using perfluoro-n-butyryl chloride.

CITATION LIST

Patent Literature

Patent Literature 1: JP S59-59643 A

Non-Patent Literature

Non-Patent Literature 1: Chemical reviews., 1996, vol. 96, pp. 1779-1808

SUMMARY OF INVENTION

Technical Problem

The disclosure provides a novel perfluorodiacyl peroxide. The disclosure also provides a solution containing the perfluorodiacyl peroxide, a polymerization initiator containing the perfluorodiacyl peroxide, and a method for producing a polymer with the perfluorodiacyl peroxide. The disclosure also provides a novel perfluoroacyl chloride.

Solution to Problem

The disclosure provides a perfluorodiacyl peroxide represented by the following formula (1):

$$(C_5F_{11}COO)_2 \qquad (1).$$

The disclosure also provides a solution containing the perfluorodiacyl peroxide and a solvent.

The solvent is preferably a fluorine-containing solvent.

The disclosure also provides a polymerization initiator containing the perfluorodiacyl peroxide.

The disclosure also provides a method for producing a polymer, including polymerizing a radically polymerizable monomer with the perfluorodiacyl peroxide.

The disclosure also provides a perfluoroacyl chloride represented by the following formula (2):

$$C_5F_{11}COCl \qquad (2).$$

Advantageous Effects of Invention

The disclosure can provide a novel perfluorodiacyl peroxide. The disclosure can also provide a solution containing the perfluorodiacyl peroxide, a polymerization initiator containing the perfluorodiacyl peroxide, and a method for producing a polymer with the perfluorodiacyl peroxide. The disclosure can also provide a novel perfluoroacyl chloride.

DESCRIPTION OF EMBODIMENTS

The following describes embodiments of the disclosure.

The perfluorodiacyl peroxide of the disclosure is represented by the following formula (1).

$$(C_5F_{11}COO)_2 \qquad (1)$$

The perfluorodiacyl peroxide represented by the formula (1) of the disclosure is applicable to, for example, a polymerization initiator, a radical generator, a fluoroalkylating agent, and a modifier.

In the formula (1), $C_5F_{11}$— may be either branched or linear, and is normally linear.

The perfluorodiacyl peroxide of the disclosure may be produced by the following method, for example, although not limited thereto.

First, perfluorohexanoic acid and phosphorus oxychloride are mixed. The mixture is further mixed with N,N-dimethyl formamide as a catalyst. The resulting liquid mixture is distilled, whereby a perfluoroacyl chloride represented by the following formula (2):

$$C_5F_{11}COCl \qquad (1)$$

is obtained.

Meanwhile, a flask is charged with sodium hydroxide, water, common salt, and a hydrogen peroxide solution. The contents are mixed with perfluorohexane under stirring, whereby a reaction solvent is prepared. This reaction solvent is cooled to 4° C. to −5° C. To the reaction solvent was added dropwise a mixed solution containing the above obtained perfluoroacyl chloride and perfluorohexane at a temperature in the range of 4° C. to −5° C., whereby the perfluorodiacyl peroxide is obtained.

The perfluoroacyl chloride represented by the formula (2) is also a novel compound provided by the disclosure. The perfluoroacyl chloride represented by the formula (2) is used as an intermediate for producing the perfluorodiacyl peroxide of the disclosure. The perfluoroacyl chloride is also usable as a perfluoroacylating agent.

The perfluorodiacyl peroxide of the disclosure may be used for synthesis of a compound. The disclosure also provides a compound synthesized using the perfluorodiacyl peroxide and a synthesis reaction using the perfluorodiacyl peroxide.

The perfluorodiacyl peroxide of the disclosure having the above structure is particularly suitable for a polymerization initiator, especially a polymerization initiator used for polymerization of a fluoromonomer.

The perfluorodiacyl peroxide represented by the formula (1), having $C_5F_{11}$ as an alkyl group binding to a carbonyl group, advantageously tends to cause radical cleavage more easily and tends to cause polymerization at lower temperatures than a conventionally known perfluorodiacyl peroxide having $C_3F_7$.

A conventionally known perfluorodiacyl peroxide having $C_7F_{15}$ is inappropriate for acquisition as a raw material and for use thereof because it causes environmental load.

The perfluorodiacyl peroxide represented by the formula (1) of the disclosure is quite a useful compound because it exhibits sufficient reactivity even at low temperatures and achieves excellent storage stability, excellent safeness, excellent handleability, and reduced environmental load.

The disclosure provides a polymerization initiator containing the perfluorodiacyl peroxide. The polymerization initiator may be the perfluorodiacyl peroxide itself or may be in the form of solution described later. Still, the polymerization initiator is preferably in the form of solution in terms of safeness.

The solution of the disclosure contains the perfluorodiacyl peroxide and a solvent.

In the solution of the disclosure, the amount of the perfluorodiacyl peroxide may be appropriately set according to the intended use and may be 1 to 50% by mass of the whole solution, for example.

For the use of the solution of the disclosure as a polymerization initiator, the amount of the perfluorodiacyl peroxide is preferably 3 to 30% by mass, more preferably 5 to 20% by mass, of the whole solution.

The solvent is not limited and may be any solvent that dissolves the perfluorodiacyl peroxide. It may be either a fluorine-free solvent or a fluorine-containing solvent.

Examples of the fluorine-free solvent include conventionally known solvents such as fluorine-free organic solvents including alcohols, ethers, and ketones.

In order to reduce a side reaction caused by chain transfer, the solvent to be used with the perfluorodiacyl peroxide is preferably a fluorine-containing solvent.

The fluorine-containing solvent is preferably, but not limited to, a solvent containing a fluorine atom in the molecule and having a boiling point of 25° C. to 100° C.

The fluorine-containing solvent may be either aromatic or aliphatic.

Examples of the fluorine-containing solvent include, but are not limited to, a perfluorocarbon, a hydrochlorofluorocarbon, a hydrofluorocarbon, a fluorine-containing ether, and perfluorobenzene. Preferred among these is at least one selected from the group consisting of a perfluorocarbon, a hydrochlorofluorocarbon, a hydrofluorocarbon, and a fluorine-containing ether, more preferred are a perfluorocarbon, a hydrofluorocarbon, and a fluorine-containing ether, and still more preferred are a hydrofluorocarbon and a fluorine-containing ether.

Examples of the perfluorocarbon include perfluorohexane, perfluoropentane, perfluoroheptane, and perfluorooctane.

An example of the fluorine-containing ether is, but not limited to, a fluorine-containing ether represented by the formula (4):

$$Rf-O-R \tag{4}$$

wherein Rf is a C2-C6 fluoroalkyl or alkyl group, and R is a C1-C4 fluoroalkyl group or a C1-C4 alkyl group, provided that the total number of carbon atoms in Rf and R is at most 8.

Rf in the formula (4) is preferably a C2-C5 fluoroalkyl group or a C2-C5 alkyl group, more preferably a C3-C4 fluoroalkyl group, still more preferably a C4 fluoroalkyl group.

R in the formula (4) is preferably a C1-C3 fluoroalkyl group or a C1-C3 alkyl group, more preferably a C1 or C2 alkyl group, still more preferably a C1 alkyl group.

In Rf and R in the formula (4), the total number of carbon atoms is preferably 3 to 7, more preferably 4 to 6, still more preferably 5.

In the fluorine-containing ether, the total number of fluorine atoms is preferably 50% or more, more preferably 60% or more, still more preferably 70% or more, relative to the total number of hydrogen atoms and fluorine atoms.

The fluorine-containing ether preferably includes at least one selected from the group consisting of a fluorine-containing ether represented by the following formula (5-1):

$$F(CF_2)_pO(CH_2)_qH \tag{5-1}$$

(wherein p is an integer of 2 to 6, and q is an integer of 1 to 4), a fluorine-containing ether represented by the following formula (5-2):

$$H(CF_2)_pO(CF_2)_qF \tag{5-2}$$

(wherein p is an integer of 2 to 6, and q is an integer of 1 to 4), a fluorine-containing ether represented by the following formula (5-3):

$$H(CF_2)_pO(CH_2)_qH \tag{5-3}$$

(wherein p is an integer of 2 to 6, and q is an integer of 1 to 4), a fluorine-containing ether represented by the following formula (5-4):

$$X(CF_2)_pCH_2O(CF_2)_qH \tag{5-4}$$

(wherein X is a fluorine atom or a hydrogen atom, p is an integer of 1 to 5, and q is an integer of 1 to 4), $(CF_3)_2CHOCH_3$, $(CF_3)_2CFOCH_3$, $CHF_2CF_2CH_2OCF_2CHF_2$, $CF_3CHFCF_2OCH_3$, and $CF_3CHFCF_2OCF_3$.

More preferred are $C_4F_9OCH_3$, $C_4F_9OC_2H_5$, $C_3CHFCH_2OCH_3$, and $(CF_3)_2CFOCH_3$, and still more preferred is $C_4F_9OCH_3$.

The fluorine-containing ether preferably has a boiling point of −20° C. to 85° C., more preferably 0° C. to 85° C., still more preferably 4° C. to 85° C.

The solution of the disclosure may contain a different additive in addition to the perfluorodiacyl peroxide and the solvent. Examples of the different additive include $C_5F_{11}COOH$ and $HC_6F_{12}COOH$.

The amount of the different additive is, for example, 0.1 to 30% by mass of the whole solution.

The method for producing a polymer of the disclosure includes polymerizing a radically polymerizable monomer with the perfluorodiacyl peroxide.

In such a method for producing a polymer, the perfluorodiacyl peroxide acts as a polymerization initiator.

The polymer may be either a crystalline polymer or an amorphous polymer. The crystalline polymer is a polymer having a melting point due to melting of crystals, while an amorphous polymer is a polymer having no clear melting point due to melting of crystals.

The perfluorodiacyl peroxide of the disclosure is suitably used as a polymerization initiator for producing a resin by means of a radical polymerization reaction at low temperatures, and is also less likely to cause chain transfer for producing a resin.

The radically polymerizable monomer is not limited and may be a conventionally known monomer. Examples thereof include non-fluorinated monomers such as ethylene and propylene and fluoromonomers such as tetrafluoroethylene, hexafluoropropylene, and alkyl vinyl ether.

The perfluorodiacyl peroxide has good compatibility with fluorine-containing solvents often used for production of a fluoropolymer and is less likely to cause chain transfer. Accordingly, it is particularly suitably used as a polymerization initiator for producing a fluoropolymer by polymerizing a fluoromonomer.

Examples of the polymerization include solution polymerization, bulk polymerization, suspension polymerization, supercritical polymerization, and emulsion polymerization.

The fluoromonomer is not limited and preferably includes at least one fluoromonomer selected from the group consisting of tetrafluoroethylene (TFE), hexafluoropropylene (HFP), vinylidene fluoride (VdF), chlorotrifluoroethylene (CTFE), perfluoro(methyl vinyl ether), perfluoro(ethyl vinyl ether), perfluoro(propyl vinyl ether), trifluoroethylene, vinyl fluoride, a perfluoro(alkyl vinyl ether) represented by the formula (6-1):

$$CF_2=CFO(CF_2CF(Y)O)_m(CF_2)_nF \qquad (6\text{-}1)$$

(wherein Y is a fluorine atom or a trifluoromethyl group, m is an integer of 0 to 2, and n is an integer of 1 to 4), a monomer represented by the formula (6-2):

$$CH_2=CF(CF_2)_nZ \qquad (6\text{-}2)$$

(wherein Z is a fluorine atom or a hydrogen atom, and n is an integer of 1 to 8), and a monomer represented by the formula (6-3):

$$CH_2=CH(CF_2)_nZ \qquad (6\text{-}3)$$

(wherein Z is a fluorine atom or a hydrogen atom, and n is an integer of 1 to 8).

The fluoromonomer may be a fluorine-containing monomer containing a hydrolyzable functional group.

The fluorine-containing monomer containing a hydrolyzable functional group is preferably a monomer represented by the following formula (7):

$$CR^{11}R^{12}=CR^{13}(CR^{14}R^{15})_a-(O)_b-R^{10}-Z \qquad (7)$$

(wherein $R^{11}$, $R^{12}$, $R^{13}$, $R^{14}$, and $R^{15}$ are the same as or different from each other and are each F or a C1-C3 perfluoroalkyl group; $R^{10}$ is a linear or branched C1-C8 perfluoroalkylene group optionally containing an oxygen atom in the main chain; a is an integer of 0 to 6; b is an integer of 0 or 1; and Z is a hydrolyzable functional group).

The fluorine-containing monomer containing a hydrolyzable functional group is more preferably a monomer having any one of the following structures (7-1) to (7-3):

$$CF_2=CF-(CF_2)_c-Z \qquad (7\text{-}1)$$

$$CF_2=CF-(CF_2C(CF_3)F)_d-Z \qquad (7\text{-}2)$$

$$CF_2=CF(CF_2)_e-O-(CF_2CFXO)_f-(CF_2)_g-Z \qquad (7\text{-}3)$$

(wherein X is F or —$CF_3$, c is an integer of 0 to 8, d is an integer of 1 or 2, e is an integer of 0 to 2, f is an integer of 0 to 3, g is an integer of 1 to 8, and Z is a hydrolyzable functional group).

Preferred examples of Z include —$SO_2F$, —$SO_2Cl$, —$COOA^1$, and —$PO_3A^2A^3$ (wherein $A^1$ is a fluoroalkyl group, and $A^2$ and $A^3$ are the same as or different from each other and are each a fluoroalkyl group).

The fluorine-containing monomer containing a hydrolyzable functional group is still more preferably a monomer represented by one of the following formulas.

$$CF_2=CF-SO_2F$$

$$CF_2=CFCF_2-SO_2F$$

$$CF_2=CFOCF_2CF_2SO_2F$$

$$CF_2=CFOCF_2CF_2CF_2CF_2SO_2F$$

$$CF_2=CFCF_2OCF_2CF_2SO_2F$$

$$CF_2=CFOCF_2CF(CF_3)OCF_2CF_2SO_2F$$

$$CF_2=CFOCF_2CF_2COOCH_3$$

$$CF_2=CFOCF_2CF(CF_3)OCF_2CF_2COOCH_3$$

The fluoromonomer may be a monomer having a cyclic structure or a cyclopolymerizable monomer.

Examples of the cyclic monomer include perfluoro(2,2-dimethyl-1,3-dioxole), perfluoro(1,3-dioxole), perfluoro(2-methylene-4-methyl-1,3-dioxolane), and 2,2,4-trifluoro-5-trifluoromethoxy-1,3-dioxole.

Examples of the cyclopolymerizable monomer include perfluoro(3-butenyl vinyl ether), perfluoro[(1-methyl-3-butenyl)vinyl ether], perfluoro(allyl vinyl ether), and 1,1-[(difluoromethylene)bis(oxy)][1,2,2-trifluoroethene].

In the formula (6-1), m is preferably an integer of 0 or 1, more preferably 0, and n is preferably an integer of 1 to 3.

In the formula (6-2), Z is preferably a hydrogen atom, and n is preferably an integer of 1 to 6, more preferably an integer of 1 to 4.

In the formula (6-3), Z is preferably a fluorine atom, and n is preferably an integer of 1 to 6, more preferably an integer of 1 to 4.

The fluoropolymer is preferably a fluororesin. The fluororesin is not limited as long as it has a polymerized unit derived from a fluorine-containing monomer.

The fluoropolymer is preferably a fluoropolymer having a polymerized unit derived from at least one fluoromonomer selected from the group consisting of tetrafluoroethylene (TFE), hexafluoropropylene (HFP), vinylidene fluoride (VdF), chlorotrifluoroethylene (CTFE), (perfluoromethyl) vinyl ether, (perfluoroethyl)vinyl ether, (perfluoropropyl) vinyl ether, trifluoroethylene, vinyl fluoride, a perfluoro (alkyl vinyl ether) represented by the following formula (6-1):

$$CF_2=CFO(CF_2CF(Y)O)_m(CF_2)_nF \qquad (6\text{-}1)$$

(wherein Y is a fluorine atom or a trifluoromethyl group, m is an integer of 0 to 2, and n is an integer of 1 to 4), a monomer represented by the following formula (6-2):

$$CH_2=CF(CF_2)_nZ \qquad (6\text{-}2)$$

(wherein Z is a fluorine atom or a hydrogen atom, and n is an integer of 1 to 8), and a monomer represented by the following formula (6-3):

$$CH_2=CH(CF_2)_nZ \qquad (6\text{-}3)$$

(wherein Z is a fluorine atom or a hydrogen atom, and n is an integer of 1 to 8).

The polymerized unit derived from a monomer used herein represents a form in which a carbon-carbon unsaturated double bond in a monomer molecule is replaced by a single bond.

The fluoropolymer may have a polymerized unit derived from a non-fluorinated monomer. In a preferred embodiment, the fluoropolymer has a polymerized unit derived from at least one non-fluorinated monomer selected from the group consisting of ethylene (Et), propylene, 1-butene, 2-butene, alkyl vinyl ether, vinyl chloride, vinylidene chloride, and an unsaturated carboxylic acid.

Examples of the fluoropolymer include, but are not limited to, polytetrafluoroethylene (PTFE), a TFE/HFP copolymer [FEP], a TFE/HFP-based copolymer (FEP) such as TFE/HFP/perfluoro(alkyl vinyl ether), a TFE/perfluoro(alkyl vinyl ether) copolymer (PFA), an Et/TFE copolymer (ETFE), a TFE/HFP/VdF copolymer (THV), a VdF/TFE copolymer (VT), polyvinylidene fluoride (PVdF), polychlorotrifluoroethylene (PCTFE), and a CTFE/perfluoro(alkyl vinyl ether)/TFE copolymer (CPT). The fluoropolymer is more preferably a melt-processable fluoropolymer.

The ETFE preferably has an Et unit:TFE unit mole ratio of 20:80 to 80:20. The Et unit:TFE unit mole ratio is more preferably 35:65 to 55:45. ETFE is a copolymer having a polymerized unit derived from TFE, a polymerized unit derived from Et, and optionally a polymerized unit derived from a different fluoromonomer or non-fluorinated monomer.

The different fluoromonomer or non-fluorinated monomer is not limited as long as it is capable of being added to both Et and TFE. Examples thereof allowing easy use include C3-C10 fluorine-containing vinyl monomers such as hexafluoroisobutylene, $CH_2=CFC_3F_6H$, and HFP. A preferred embodiment among these is a fluorine-containing vinyl monomer represented by the following formula (8):

$$CH_2=CH-Rf^4 \quad (8)$$

(wherein $Rf^4$ is a C4-C8 perfluoroalkyl group). An example of the non-fluorinated monomer is a vinyl monomer represented by the following formula (9):

$$CH_2=CH-R^4 \quad (9)$$

(wherein $R^4$ may have any carbon number, may contain an aromatic ring, and may contain a carbonyl group, an ester group, an ether group, an amide group, a cyano group, a hydroxyl group, or an epoxy group, and $R^4$ contains no fluorine atom).

Another preferred embodiment is that ETFE is an Et/TFE/HFP copolymer (EFEP). ETFE may further have a polymerized unit derived from a different fluoromonomer other than HFP or a different non-fluorinated monomer. The different fluoromonomer or non-fluorinated monomer is preferably used in an amount of 10 mol % or less, more preferably 5 mol % or less of the entire polymer. The mole ratio of Et unit:TFE unit:a monomer unit derived from a different fluoromonomer or non-fluorinated monomer is preferably (31.5 to 54.7):(40.5 to 64.7):(0.5 to 10).

The FEP preferably has a HFP unit in an amount of more than 2% by mass and 20% by mass or less, more preferably 8% to 15% by mass.

The perfluoro(alkyl vinyl ether) for the PFA is preferably one containing a C1-C6 alkyl group, more preferably perfluoro(methyl vinyl ether), perfluoro(ethyl vinyl ether), or perfluoro(propyl vinyl ether). The PFA preferably has a perfluoro(alkyl vinyl ether) unit in an amount of more than 2% by mass and 15% by mass or less, more preferably 2.5% to 8.0% by mass.

The FEP and PFA each may be further polymerized with a different monomer as long as they have the above composition. The different monomer may be perfluoro(alkyl vinyl ether) for the FEP and may be HFP for the PFA, for example. One different monomer may be used or two or more thereof may be used.

The amount of the different monomer to be polymerized with the FEP or PFA depends on the type thereof and is usually preferably 2% by mass or less, more preferably 1.5% by mass or less, of the resulting fluoropolymer.

The amounts of the monomer units of the above copolymers can be calculated by appropriately combining any of NMR, FT-IR, elementary analysis, and X-ray fluorescence analysis according to the types of the monomers.

The polymerization can be performed in a polymerization solvent. The polymerization solvent is not limited and may be, for example, one of the exemplified fluorine-free solvents and fluorine-containing solvents usable for the solution of the disclosure. In order to efficiently producing a fluoropolymer, a fluorine-containing solvent is preferred. The polymerization solvent is preferably the aforementioned fluorine-containing solvent. In particular, preferred examples thereof include at least one selected from the group consisting of a perfluorocarbon, a hydrochlorofluorocarbon, a hydrofluorocarbon, and a fluorine-containing ether, still more preferred examples include a perfluorocarbon, a hydrofluorocarbon, and a fluorine-containing ether, and further more preferred examples include a hydrofluorocarbon and a fluorine-containing ether.

Production of the polymer may be performed using the perfluorodiacyl peroxide of the disclosure. This polymerization can provide a wet fluoropolymer that is made wet by a substance such as a polymerization solvent.

In other words, this polymerization reaction can provide a wet fluoropolymer including a fluoropolymer and a solvent.

The polymerization may be performed in the following way, for example. A reaction vessel is charged with a polymerization solvent, a fluoromonomer, and optionally an additive. The contents in the reaction vessel are stirred, the reaction vessel is maintained at a predetermined polymerization temperature, and a predetermined amount of perfluorodiacyl peroxide is fed to initiate a polymerization reaction. Additives such as a surfactant, a chain transfer agent, and a radical scavenger may also be fed to the vessel. The polymerization may be performed by batch polymerization, semi-batch polymerization, or continuous polymerization. The materials for the polymerization reaction may be fed in an intermittent manner or a continuous manner after the starting of the polymerization reaction.

The perfluorodiacyl peroxide may be fed to the reaction vessel in a solution state dissolved in a polymerization solvent.

Examples of the chain transfer agent include hydrocarbons such as isopentane, n-pentane, n-hexane, and cyclohexane; alcohols such as methanol and ethanol; and halogenated hydrocarbons such as carbon tetrachloride, chloroform, methylene chloride, and methyl chloride.

The polymerization temperature of the polymerization reaction is not limited, and is preferably 0° C. to 100° C., more preferably 10° C. to 90° C. The polymerization pressure is not limited, and is preferably 0.1 to 10 MPa, more preferably 0.3 to 5 MPa.

The polymerization temperature indicates the temperature of the solvent in the reaction vessel, and the polymerization pressure indicates the pressure in the reaction vessel.

Use of the perfluorodiacyl peroxide represented by the formula (1) of the disclosure as a material can provide a novel compound. The novel compound can be produced by reacting the perfluorodiacyl peroxide represented by the formula (1) with a different compound, according to one of the methods disclosed in, for example, JP H04-352769 A, JP H05-001066 A, JP 3269135 B, JP H04-360891 A, JP H04-159273 A, JP H04-149192 A, JP 3032781 B, JP 2775913 B, JP H03-123751 A, and JP H03-112951 A.

The perfluorodiacyl peroxide represented by the formula (1) may also be used as a modifier. Such use may be applied to the reactions disclosed in, for example, JP H04-082860 A, JP H04-020527 A, JP H04-277586 A, JP H03-244631 A, JP H03-234706 A, and JP H02-300208 A.

EXAMPLE

The perfluorodiacyl peroxide of the disclosure is described with reference to examples, but the examples are not intended to limit the perfluorodiacyl peroxide of the disclosure.

Example 1

(Synthesis of perfluoro-n-hexyl chloride)

A 500-mL flask equipped with a mechanical stirrer, a thermometer, a dropping funnel, a distillation condenser, and an exhaust tube was charged with 471 g (1.50 mol) of perfluoro-n-hexanoic acid. To the flask was added 161 g (1.05 mol) of phosphorus oxychloride at room temperature over two minutes with the contents being stirred. No exothermal behavior was observed at this point. Then, 55 g (0.75 mol) of dimethyl formamide (DMF) was added dropwise at 5° C. over five minutes. White smoke and exothermal behavior were rarely observed at this point. After the dropwise addition, the temperature of a bath prepared for heating the flask was increased to 110° C., and then the contents in the flask were distilled through a distillation column KIRIYAMA Pac available from Kiriyama Glass Works Co. The resulting product was colorless liquid in an amount of 449 g (yield: 90%). The purity of the product was found to be 99% by $^{19}$F-NMR. The product was analyzed by infrared absorption spectrum, and absorption of carbonyl was observed at 1790 cm$^{-1}$. The above $^{19}$F-NMR and infrared absorption spectrum together with elemental analysis confirmed that the obtained product was perfluoro-n-hexyl chloride.

Example 2

(Synthesis of bis(perfluoro-n-hexyl)peroxide)

A 500-mL flask equipped with a mechanical stirrer, a thermometer, and a dropping funnel was charged with 8.8 g (0.22 mol) of sodium hydroxide and 165.0 g of water. The sodium hydroxide was dissolved in water, and then 8.2 g of common salt was added to the solution. To the flask was added 7.5 g (0.11 mol) of a 50% hydrogen peroxide solution. With the contents being stirred, 142 g of perfluorohexane was added thereto, and the reaction solution was then cooled to −5° C. The cooling was followed by dropwise addition of a mixed solution containing 43.16 g (0.13 mol) of the perfluoro-n-hexyl chloride obtained in Example 1 and having a purity of 99% and 36 g of perfluorohexane at a temperature in the range of −2° C. to −5° C.

The mixture was aged for 60 minutes, followed by separation and washing with water. The resulting product was dried over magnesium sulfate. Thereby, bis(perfluoro-n-hexyl)peroxide was obtained in an amount of 195 g at a yield of 48% at a purity of 10.0 wt %.

The analysis of the peroxide was performed in accordance with "New Experimental Chemistry Course 15, Oxidation and Reduction [I-2] 11.3.3, Analysis of Peroxide: Iodine Titration (Shin-Jikken Kagaku Kouza 15, Sanka to Kangen [1-2] 11.3.3, Kasankabutsu no Bunsekihou: Youso Tekitei hou)", and thereby the yield and purity were calculated.

Example 3

A 4.1-L autoclave was charged with 1095 g of distilled water and sufficiently purged with nitrogen. To the autoclave were fed 1133 g of hexafluoropropylene (HFP) and 12.3 g of perfluoro(propyl vinyl ether) (PPVE). The temperature in the system was maintained at 32° C., and the stirring rate was maintained at 580 rpm. Then, 120 g of tetrafluoroethylene (TFE) was fed to the autoclave, and then 9.6 g of the peroxide solution synthesized in Example 2 was fed thereto to initiate polymerization. Then, 9.6 g of the peroxide solution synthesized in Example 2 was fed every two hours over the course of the polymerization. Because the pressure in the system drops with the progress of the polymerization, tetrafluoroethylene (TFE) was continuously fed to maintain the pressure in the system at 1.02 MPa. The reaction was stopped when the total amount of tetrafluoroethylene (TFE) fed reached 171 g. The reaction lasted 4.5 hours.

After the polymerization, the gas in the system was released to ordinary pressure, followed by purge with nitrogen and then opening of the autoclave. White polymer powder was taken out and dried with an electric furnace at 150° C. for 12 hours. The resulting polymer had a weight of 193 g. Composition analysis by $^{19}$F-NMR indicated that the polymer was a copolymer containing 88.4 wt % of TFE, 10.3 wt % of HFP, and 1.3 wt % of PPVE.

The melt flow rate measured at 372° C. was 7.9 g/10 min. The melt flow rate was measured at 372° C. and at a load of 5 kg in accordance with ASTM D-1238, using a die having a diameter of 2.1 mm and a length of 8 mm.

The invention claimed is:

1. A polymerization initiator comprising a solution comprising a perfluorodiacyl peroxide and a fluorine-containing solvent;
   wherein the perfluorodiacyl peroxide is represented by the following formula (1):

(C$_5$F$_{11}$COO)$_2$             (1).

wherein C$_5$F$_{11}$-is linear,
   and the fluorine-containing solvent is at least one selected from the group consisting of a perfluorocarbon, a hydrofluorocarbon, and a fluorine-containing ether.

2. A method for producing a fluoropolymer, comprising polymerizing a fluoromonomer in the presence of the polymerization initiator according to claim 1.

* * * * *